United States Patent
Kim et al.

(10) Patent No.: US 10,765,623 B2
(45) Date of Patent: Sep. 8, 2020

(54) COMPOSITION FOR PREVENTING HAIR LOSS OR PROMOTING HAIR GROWTH COMPRISING EXTRACELLULAR FOLLICLE DERIVED FROM LACTIC ACID BACTERIA

(71) Applicant: AMOREPACIFIC CORPORATION, Seoul (KR)

(72) Inventors: Sung Tae Kim, Yongin-si (KR); Yonghee Lee, Yongin-si (KR); Seung Hyun Shin, Yongin-si (KR); Hyun Gee Lee, Yongin-si (KR); Eun-Gyung Cho, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 41 days.

(21) Appl. No.: 15/760,908

(22) PCT Filed: Sep. 26, 2016

(86) PCT No.: PCT/KR2016/010750
§ 371 (c)(1),
(2) Date: Mar. 16, 2018

(87) PCT Pub. No.: WO2017/057882
PCT Pub. Date: Apr. 6, 2017

(65) Prior Publication Data
US 2018/0256490 A1    Sep. 13, 2018

(30) Foreign Application Priority Data

Sep. 30, 2015 (KR) .................. 10-2015-0137862

(51) Int. Cl.
| | | |
|---|---|---|
| *A61K 8/00* | (2006.01) | |
| *A61K 8/18* | (2006.01) | |
| *A61K 9/00* | (2006.01) | |
| *A01N 63/00* | (2020.01) | |
| *A01N 65/00* | (2009.01) | |
| *A61K 51/00* | (2006.01) | |
| *A61M 36/14* | (2006.01) | |
| *A61K 8/99* | (2017.01) | |
| *A61Q 7/00* | (2006.01) | |
| *A61K 35/744* | (2015.01) | |
| *A61K 35/745* | (2015.01) | |
| *A61K 35/747* | (2015.01) | |
| *A61P 17/14* | (2006.01) | |
| *A61K 8/14* | (2006.01) | |

(52) U.S. Cl.
CPC .................. *A61K 8/99* (2013.01); *A61K 8/14* (2013.01); *A61K 35/744* (2013.01); *A61K 35/745* (2013.01); *A61K 35/747* (2013.01); *A61P 17/14* (2018.01); *A61Q 7/00* (2013.01)

(58) Field of Classification Search
CPC .......... A61Q 5/12; A61K 35/12; A61K 35/74; A61K 51/1234
See application file for complete search history.

(56) References Cited

U.S. PATENT DOCUMENTS

| | | | |
|---|---|---|---|
| 6,376,557 B1 | 4/2002 | Zaveri | |
| 7,759,105 B2 | 7/2010 | Cobb et al. | |
| 8,969,653 B2 * | 3/2015 | Gho ..................... | C12Q 1/6883 424/234.1 |
| 9,273,359 B2 | 3/2016 | Gho et al. | |
| 2011/0064777 A1 * | 3/2011 | Mohan ................... | A61K 8/986 424/401 |
| 2011/0064832 A1 * | 3/2011 | Burke-Colvin ........ | A61K 8/585 424/727 |
| 2012/0159658 A1 | 6/2012 | Gho et al. | |
| 2014/0023618 A1 | 1/2014 | Goren et al. | |

FOREIGN PATENT DOCUMENTS

| | | | |
|---|---|---|---|
| EP | 1097700 A1 * | 5/2001 | |
| EP | 2484752 * | 8/2012 | |
| GB | 2466195 A | 6/2010 | |
| JP | 2007-527213 A | 9/2007 | |
| JP | 2015-059094 A | 3/2015 | |
| JP | 2016-117683 A | 6/2016 | |
| KR | 10-2011-0025603 A | 3/2011 | |

(Continued)

OTHER PUBLICATIONS

WebMD, https://www.webmd.com/skin-problems-and-treatments/hair-loss/understanding-hair-loss-prevention, accessed on Jan. 7, 2019 (Year: 2019).*

(Continued)

*Primary Examiner* — Gary B Nickol
*Assistant Examiner* — Lakia J Jackson-Tongue
(74) *Attorney, Agent, or Firm* — Merchant & Gould P.C.

(57) ABSTRACT

The present specification discloses a composition for preventing hair loss or promoting hair growth comprising, as an active ingredient, extracellular follicles derived from lactic acid bacteria, and a method for preparing the extracellular follicles derived from lactic acid bacteria. The composition has an effect of preventing and prohibiting hair from falling off from the scalp or becoming thin or tapered. In addition, the composition has an effect of implementing a hair growth function for generating new hair, or a function for promoting the hair growth, as well as a function of promoting a delay from an anagen to a catagen phase of a hair cycle and a function of growing the existing hair healthy.

7 Claims, 7 Drawing Sheets

(56) References Cited

FOREIGN PATENT DOCUMENTS

| KR | 10-2015-0067058 A | 6/2015 |
|---|---|---|
| WO | 2005/002361 A1 | 1/2005 |
| WO | 2011/027956 A2 | 3/2011 |
| WO | 2011/027990 A2 | 3/2011 |

OTHER PUBLICATIONS

Mayo Clinic, https://www.mayoclinic.org/diseases-conditions/hair-loss/diagnosis-treatment/drc-20372932, accessed on Jan. 7, 2019 (Year: 2019).*

WebMD, https://www.webmd.com/skin-problems-and-treatments/hair-loss/infectious-agents#1, Published on Mar. 1, 2010 (Year: 2010).*

International Search Report from PCT/KR2016/010750 (dated Jan. 11, 2017).

Written Opinion from PCT/KR2016/010750 (dated Jan. 11, 2017).

Bang et al., "Exosomes: New players in cell-cell communication", The International Journal of Biochemistry and Cell Biology, 44:2060-2064 (2012).

Camussi et al., "Exosomes/microvesicles as a mechanism of cell-to-cell communication", Kidney International, 78:838-848 (2010).

Kim et al., "EVpedia: A community web resource for prokaryotic and eukaryotic extracellular vesicles research", Seminars in Cell & Developmental Biology, 40:4-7 (2015).

Kim et al., "Gram-negative and Gram-positive bacterial extracellular vesicles", Seminars in Cell & Developmental Biology, 40:97-104 (2015).

Loyer et al., "Microvesicles as Cell—Cell Messengers in Cardiovascular Diseases", Circulation Research, 114 (2):345-353 (Jan. 2014).

Ohno et al., "Roles of exosomes and microvesicles in disease pathogenesis", Advanced Drug Delivery Reviews, 65 (3):398-401 (2013).

Extended European Search Report from European Application No. 16852028.6, dated Mar. 14, 2019.

Jeroen Van Bergenhenegouwen et al: "Extracellular Vesicles Modulate Host-Microbe Responses by Altering TLR2 Activity and Phagocytosis", PLOS ONE, vol . 9, No. 2, Feb. 1, 2014 (Feb. 1, 2014), pp. 1-11, XP55312063.

Office Action from corresponding Japanese Application No. 2018-516427, dated Jun. 9, 2020.

* cited by examiner

[Fig. 1]
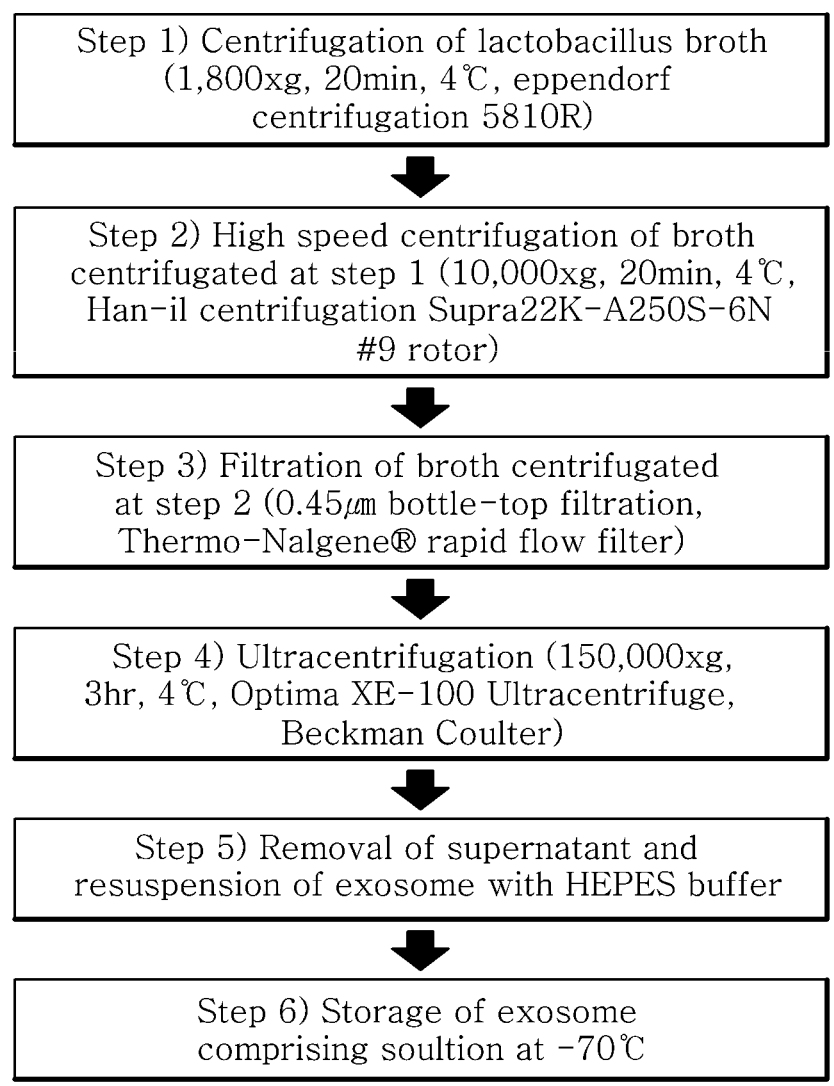

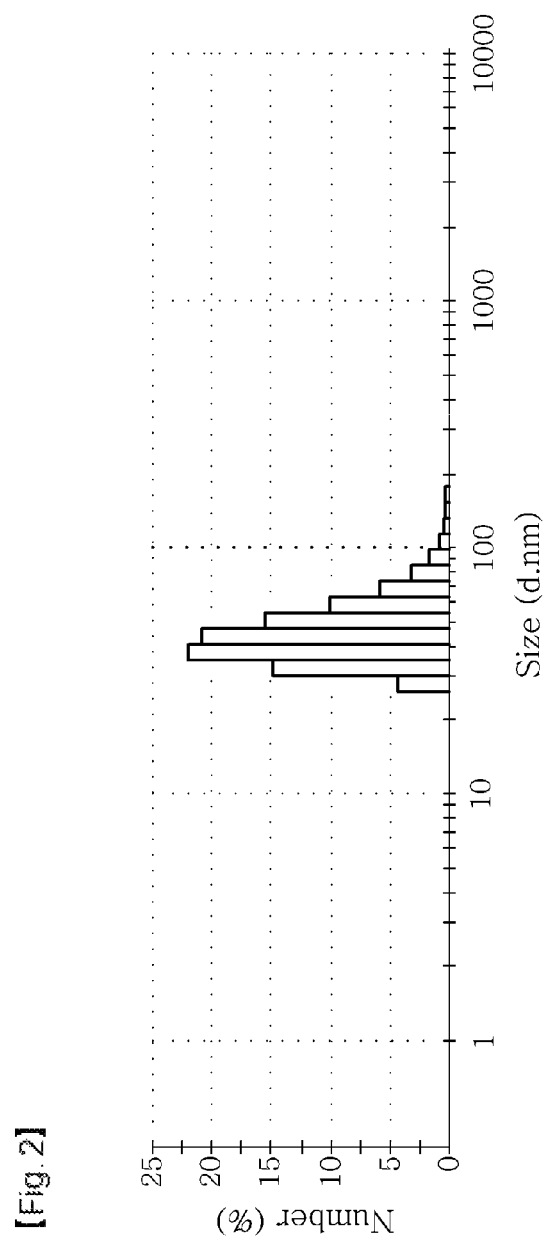
[Fig. 2]

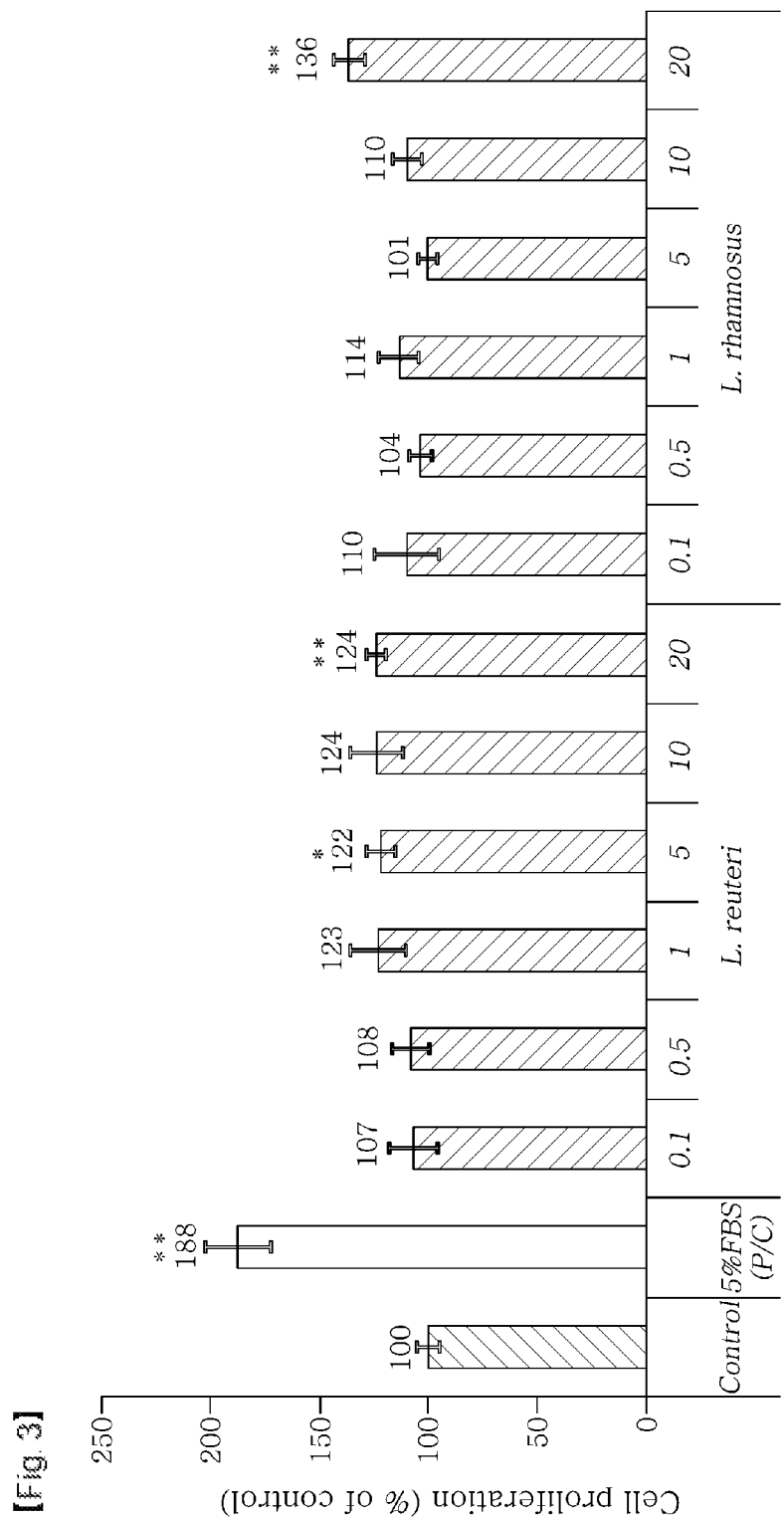
[Fig. 3]

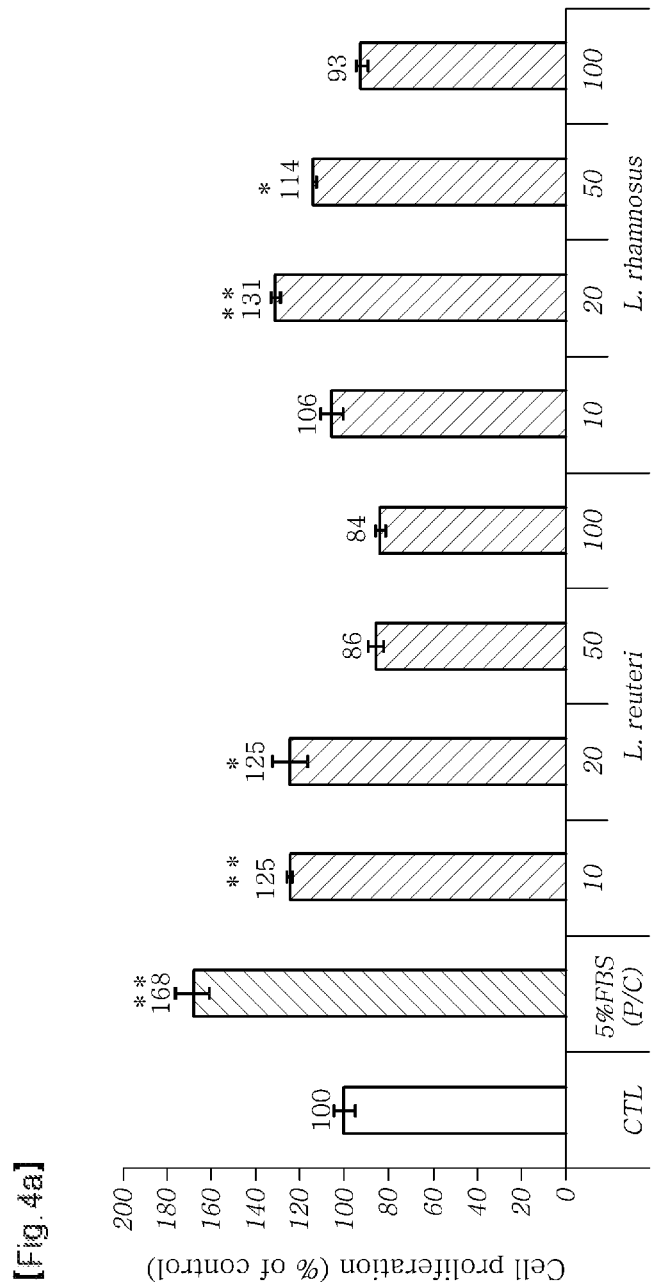
[Fig. 4a]

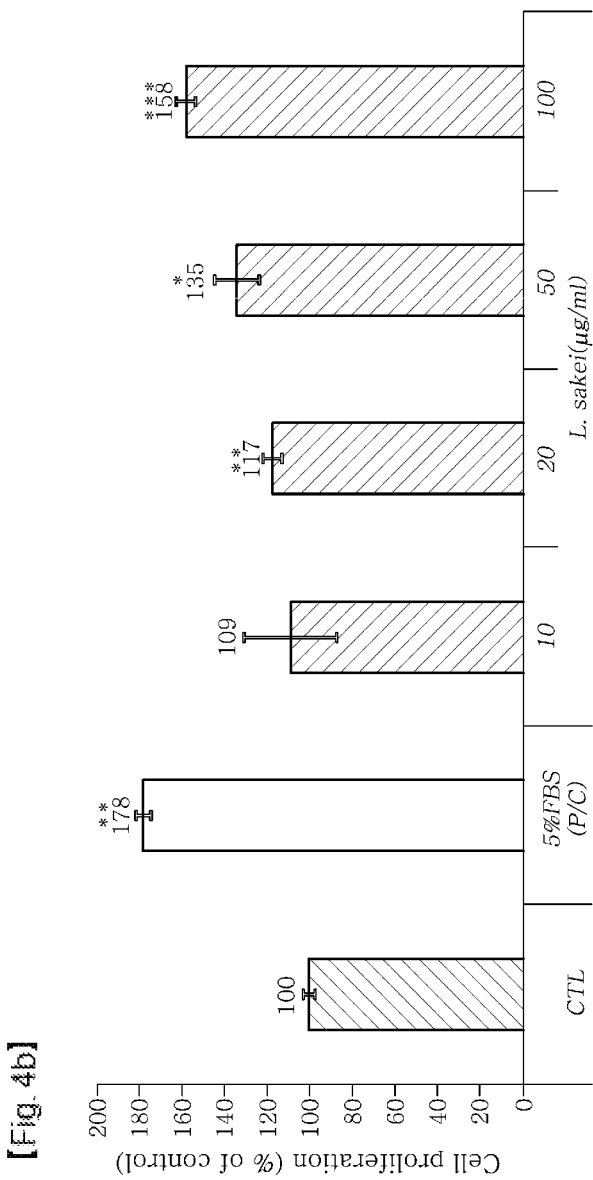

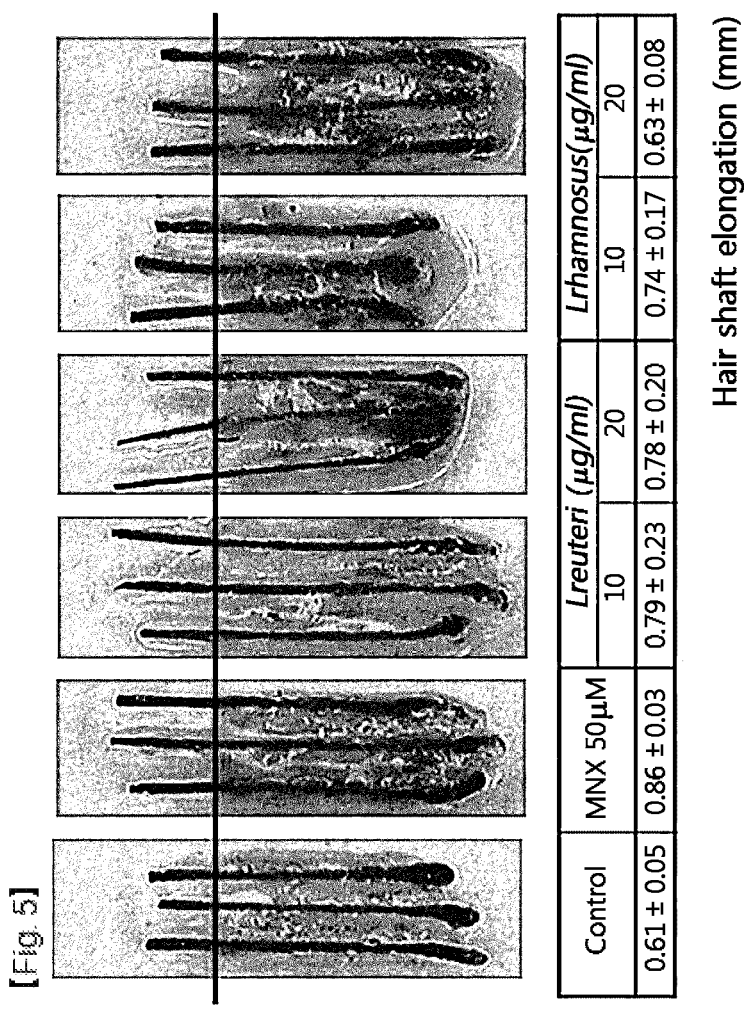

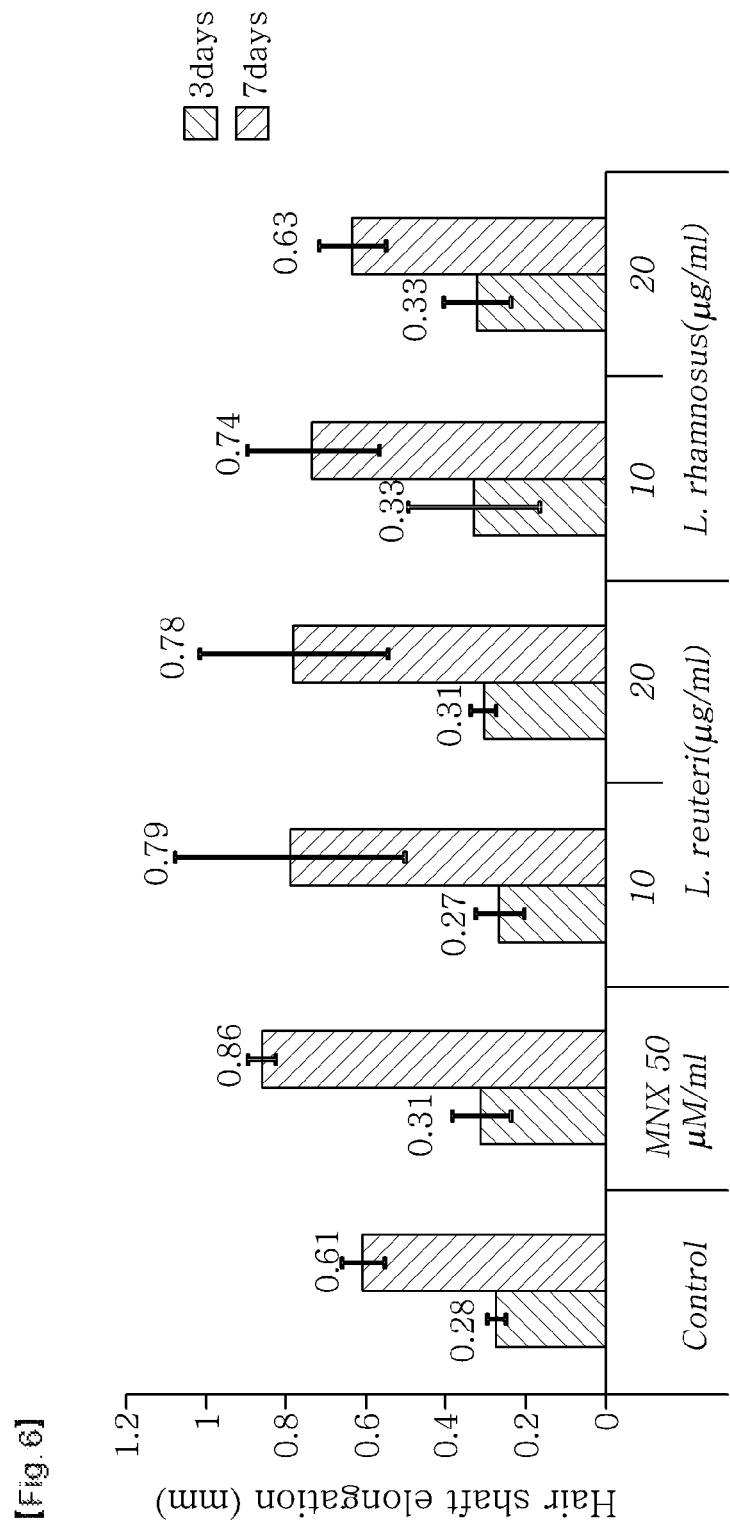
[Fig. 6]

COMPOSITION FOR PREVENTING HAIR LOSS OR PROMOTING HAIR GROWTH COMPRISING EXTRACELLULAR FOLLICLE DERIVED FROM LACTIC ACID BACTERIA

This application is a U.S. National Stage Application under 35 U.S.C. § 371 of International Patent Application No. PCT/KR2016/010750 filed Sep. 26, 2016, which claims the benefit of priority to Korean Patent Application No. 10-2015-0137862 filed Sep. 30, 2015, the disclosures of all of which are hereby incorporated by reference in their entireties. The International Application was published in Korean on Apr. 6, 2017 as WO 2017/057882.

TECHNICAL FIELD

Disclosed in the present disclosure are a composition for preventing hair loss or promoting hair growth, which contains lactic acid bacteria-derived extracellular vesicles as an active ingredient, and a method for preparing the lactic acid bacteria-derived extracellular vesicles.

BACKGROUND

Most animal cells have the ability of secreting cell-derived extracellular vesicles of various sizes and compositions. These extracellular vesicles are found in all biological fluids, including blood, urine, saliva and cultured medium of cell cultures (Loyer X, Vion A C, Tedgui A, Boulanger C M. Microvesicles as cell-cell messengers in cardiovascular diseases. *Circ Res* 2014; 114: 345-53; Ohno S, Ishikawa A, Kuroda M. Roles of exosomes and microvesicles in disease pathogenesis. *Adv Drug Deliv Rev* 2013; 65: 398-401).

Extracellular vesicles are membrane structure vesicles with diameters from about 20 nm to about 5 µm. They differ in sizes and compositions and include various species such as exosomes (about 30-100 nm), ectosomes, microvesicles (about 100-1,000 nm), microparticles, etc.

The different types of the extracellular vesicles are distinguished based on their origin, diameter, density in sucrose, shape, precipitation rate, lipid composition, protein marker, secretion type (i.e., whether they are induced by signals or naturally produced), etc. For example, microvesicles are membrane vesicles ranging from about 100 to 1,000 nm with irregular shapes. They originate from the plasma membrane and are known to contain integrins, selectins, markers including CD40 ligand, etc., and phospholipids including phosphatidylserines. And, exosomes are the smallest membrane vesicles ranging from about 30 to 100 nm (<200 nm) with a cups shape. They originate from endosomes and are known to contain tetraspanins such as CD63 and CD9, markers including TSG101 and ESCRT, and lipids including cholesterols, sphingomyelins, ceramides and phosphatidylserines.

The extracellular vesicles reflect the state of the cells (donor cells) from which they are secreted, exhibit various biological activities depending on the cells from which they are secreted, and play an important role in cell-to-cell interactions (cell-to-cell communications) as they transfer genetic materials and proteins between cells.

Prokaryotic cells and eukaryotic cells are also known to secret extracellular vesicles (Camussi, G., Deregibus, M. C., Bruno, S., Cantaluppi, V., & Biancone, L. (2010). Exosomes/microvesicles as a mechanism of cell-to-cell communication. *Kidney International*, 78(9), 838-848; Bang, Claudia, and Thomas Thum. "Exosomes: New players in cell-cell communication." *The International Journal of Biochemistry & Cell Biology* 44.11 (2012): 2060-2064; Kim, D. K., Lee, J., Simpson, R. J., Lötvall, J., & Gho, Y. S. (2015, April). EVpedia: A community web resource for prokaryotic and eukaryotic extracellular vesicles research. *Seminars in Cell & Developmental Biology* (Vol. 40, pp. 4-7). Academic Press; Kim, J. H., Lee, J., Park, J., & Gho, Y. S. (2015, April). Gram-negative and Gram-positive bacterial extracellular vesicles. *Seminars in Cell & Developmental Biology* (Vol. 40, pp. 97-104). Academic Press). Meanwhile, lactic acid bacteria, which are the representative beneficial bacteria for human, are bacteria which produce organic acids such as lactic acid or acetic acid by degrading sugars such as glucose or lactose. They are used in preparing fermented foods such as fermented milk, cheese or butter through the fermentation process of producing organic acids from sugars, but there have been few researches on the particular use of extracellular vesicles derived therefrom. The prior art about bacteria-derived extracellular vesicles is disclosed in Korean Patent Publication No. 10-2011-0025603.

DISCLOSURE

Technical Problem

In an aspect, the present disclosure is directed to providing a composition for preventing hair loss or promoting hair growth, which contains lactic acid bacteria-derived extracellular vesicles as complex physiologically active substances as an active ingredient.

In another aspect, the present disclosure is directed to providing a method for preparing the lactic acid bacteria-derived extracellular vesicles.

Technical Solution

The present disclosure provides a composition for preventing hair loss or promoting hair growth, which contains lactic acid bacteria-derived extracellular vesicles as an active ingredient.

In an aspect, the lactic acid bacterium may include one or more selected from a group consisting of the bacteria in the genera *Bifidobacterium*, *Lactobacillus*, *Streptococcus*, *Leuconostoc*, *Pediococcus* and *Lactococcus*.

In another aspect, the lactic acid bacterium may include a bacterium in the genus *Lactobacillus*.

In another aspect, the bacterium in the genus *Lactobacillus* may include one or more selected from a group consisting of *Lactobacillus reuteri* (*L. reuteri*), *Lactobacillus rhamnosus* (*L. rhamnosus*) and *Lactobacillus sakei* (*L. sakei*).

In another aspect, the extracellular vesicle may be isolated from a culture of lactic acid bacteria.

In another aspect, the extracellular vesicle may be an exosome-like vesicle.

In another aspect, the extracellular vesicle may have a diameter of 20-500 nm.

In another aspect, the extracellular vesicle may precipitate when a culture of lactic acid bacteria is ultracentrifuged at 100,000×g or higher.

In another aspect, the active ingredient may induce hair growth by activating dermal papilla cells (DPCs).

The present disclosure also provides a method for preparing the lactic acid bacteria-derived extracellular vesicles, which includes: (1) a step of obtaining a supernatant by centrifuging a culture of lactic acid bacteria; (2) a step of filtering the obtained supernatant; and (3) a step of obtaining precipitates by ultracentrifuging the obtained filtrate.

In an aspect, the centrifugation in the step (1) may be performed at 1,000-20,000×g.

In another aspect, the ultracentrifugation in the step (3) may be performed at 100,000×g or higher.

In another aspect, the method may further include, after the step (3), (4) a step of suspending the obtained precipitates.

Advantageous Effects

In an aspect, the present disclosure provides an effect of providing a composition for preventing hair loss or promoting hair growth, which contains lactic acid bacteria-derived extracellular vesicles as complex physiologically active substances as an active ingredient.

The composition for preventing hair loss or promoting hair growth provides an effect of preventing loss of hair from the scalp or thinning of hair.

The composition for preventing hair loss or promoting hair growth provides an effect of sprouting new hair, promoting the hair sprouting, promoting delay of transition from anagen to catagen in the hair growth cycle, and promoting healthy growth of existing hair.

In another aspect, the present disclosure provides an effect of providing a method for preparing the lactic acid bacteria-derived extracellular vesicles.

BRIEF DESCRIPTION OF DRAWINGS

FIG. 1 shows a process of isolating extracellular vesicles from lactic acid bacteria according to an exemplary embodiment of the present disclosure.

FIG. 2 shows a result of measuring the size of isolated lactic acid bacteria-derived extracellular vesicles of according to an exemplary embodiment of the present disclosure.

FIG. 3 shows a result of measuring the proliferation of dermal papilla cells treated with lactic acid bacteria-derived extracellular vesicles at low concentrations (0.1-20 μg/mL) according to an exemplary embodiment of the present disclosure.

FIGS. 4a and 4b show a result of measuring the proliferation of dermal papilla cells treated with lactic acid bacteria-derived extracellular vesicles at high concentrations (10-100 μg/mL) according to an exemplary embodiment of the present disclosure.

FIG. 5 shows a result of measuring hair shaft elongation after treating a hair follicle organ culture with lactic acid bacteria-derived extracellular vesicles according to an exemplary embodiment of the present disclosure.

FIG. 6 shows a result of measuring hair shaft elongation after treating a hair follicle organ culture with lactic acid bacteria-derived extracellular vesicles according to an exemplary embodiment of the present disclosure.

BEST MODE

Hereinafter, the present disclosure is described in detail.

The present disclosure provides a composition for preventing hair loss or promoting hair growth, which contains lactic acid bacteria-derived extracellular vesicles as an active ingredient.

In an exemplary embodiment, the extracellular vesicle may be an exosome-like vesicle.

The hair growth cycle can be divided into three major stages known as anagen, catagen and telogen phases. In anagen, hair grows as the hair follicle grows deep into the skin. The next phase, catagen, is a transitional phase characterized by stoppage of cell division. During this procedure, the hair follicle shrinks gradually and hair growth is stopped. In the next phase, telogen, the shrunk hair follicle contains germs tightly packed with dermal papilla cells. The transition from telogen to new anagen is induced by the fast cell growth in the germs, the expansion of dermal papilla and the synthesis of hair base ingredients. In general, "hair growth" occurs in anagen and is promoted by induction of transition from telogen to anagen or by delay of transition from anagen to catagen.

In the present disclosure, "hair loss" refers to a phenomenon of loss of hair from the scalp or thinning of hair, "prevention of hair loss" refers to prevention and inhibition of the hair loss phenomenon, and "promotion of hair growth" refers not only to sprouting of new hair or promotion of the hair sprouting but also to promotion of delay of transition from anagen to catagen in the hair growth cycle, and promotion of healthy growth of existing hair.

In the present disclosure, the "extracellular vesicle" refers to a vesicle secreted by a cell to the extracellular space. The extracellular vesicle is divided into inside and outside by a lipid bilayer and contains plasma membrane lipids, plasma membrane proteins, nucleic acids, cytoplasmic components, etc. of bacteria. In general, it is smaller in size than the bacterium from which it originates, although not being limited thereto. The extracellular vesicle serves as an extracellular transporter mediating cell-cell communication by binding to other cells and transferring membrane components, mRNAs, miRNAs, etc. to the acceptor cells.

In the present disclosure, the "exosome-like vesicle" refers to a nanosized extracellular vesicle and the term is used in the broadest concept, including not only a nanosized exosome but also a vesicle similar in a nanosized vesicular structure and a composition with the exosome.

In the present disclosure, the lactic acid bacteria may be either isolated lactic acid bacteria or commercially available lactic acid bacteria.

In an exemplary embodiment, the lactic acid bacterium may include one or more selected from a group consisting of the bacteria in the genera *Bifidobacterium, Lactobacillus, Streptococcus, Leuconostoc, Pediococcus* and *Lactococcus*.

Specifically, the lactic acid bacterium may include one or more selected from a group consisting of *Bifidobacterium breve* (*B. breve*), *Bifidobacterium longum* (*B. longum*), *Bifidobacterium infantis* (*B. infantis*), *Lactobacillus bulgaricus* (*L. bulgaricus*), *Lactobacillus reuteri* (*L. reuteri*), *Lactobacillus rhamnosus* (*L. rhamnosus*), *Lactobacillus plantarum* (*L. plantarum*), *Lactobacillus sakei* (*L. sakei*), *Lactobacillus acidophilus* (*L. acidophilus*), *Streptococcus thermophilus* (*S. thermophilus*), *Streptococcus faecium* (*S. faecium*), *Streptococcus faecalis* (*S. faecalis*), *Leuconostoc mesenteroides* (*L. mesenteroides*), *Pediococcus cerevisiae* (*P. cerevisiae*) and *Lactococcus lactis* (*L. lactis*).

In an exemplary embodiment, the extracellular vesicle may be isolated from a culture of lactic acid bacteria. The extracellular vesicle may be physically isolated entirely or partially from existing tissues or cells.

In an aspect, the extracellular vesicle may have a diameter of 20-500 nm. In another aspect, the extracellular vesicle may have a diameter of 20 nm or larger, 30 nm or larger, 40 nm or larger, 50 nm or larger, 60 nm or larger, 70 nm or larger, 80 nm or larger, 90 nm or larger or 100 nm or larger and 500 nm or smaller, 450 nm or smaller, 400 nm or smaller, 350 nm or smaller, 300 nm or smaller, 250 nm or smaller, 200 nm or smaller, 150 nm or smaller or 100 nm or smaller.

In another aspect, the extracellular vesicle may be precipitated by ultracentrifuging a culture of lactic acid bacteria at 100,000×g or higher, specifically at 100,000-200,000×g, 100,000-150,000×g or 150,000-200,000×g.

In another aspect, the membrane component of the extracellular vesicle may be chemically or physically modified so as to effectively perform the desired function in a target cell. For example, the membrane component of the extracellular vesicle may be chemically modified using a thiol group (—SH) or an amine group (—$NH_2$) or by chemically binding a inducing substance, a fusogen, polyethylene glycol to the extracellular vesicle.

In an exemplary embodiment, the extracellular vesicle may be isolated by one or more method selected from a group consisting of centrifugation, ultracentrifugation, differential centrifugation, equilibrium density centrifugation, density gradient, filtration, dialysis and free-flow electrophoresis, although not being limited thereto.

Density gradient is a method which is the most frequently used when separating materials with different densities. As a specific example, density gradient separation materials such as Ficoll, glycerol, sucrose, cesium chloride, iodixanol, etc. may be used, although not being limited thereto. In an aspect, the density gradient may be used together with ultracentrifugation, etc. In another aspect, gel filtration or ultrafiltration may be used to separate the extracellular vesicles. In another aspect, dialysis may be used instead of filtration in order to remove small-sized molecules. In another aspect, free-flow electrophoresis may be used.

In an exemplary embodiment, the bacteria-derived extracellular vesicle exhibiting effective activity may be obtained by a method which includes: (1) a step of obtaining a supernatant by centrifuging a culture of lactic acid bacteria; (2) a step of filtering the obtained supernatant; and (3) a step of obtaining precipitates by ultracentrifuging the obtained filtrate.

In an exemplary embodiment, the centrifugation in the step (1) may be performed at 1,000-20,000×g, 1,500-20,000×g, 1,500-15,000×g or 1,500-10,000×g for 30-60 minutes. The speed or time of the centrifugation may be varied by stages. For example, after separating removing lactic acid bacteria from the culture by centrifuging at low speed of 1,500-2,000×g and then separating the culture supernatant from cells, the culture supernatant may be further centrifuged at high speed of 10,000-20,000×g in order to additionally remove cells, cell debris, etc.

In an exemplary embodiment, the filtration in the step (2) may be performed using a 0.3-0.5 µm sized filter. The purity of the centrifuged culture may be increased through this filtration process.

In another aspect, the ultracentrifugation in the step (3) may be performed at 100,000×g or higher, specifically at 100,000-200,000×g, 100,000-150,000×g or 150,000-200,000×g, for 1-5 hours.

In another aspect, the method may further include, after the step (3), (4) a step of suspending the obtained precipitates.

In another aspect, the present disclosure provides a method for preventing hair loss or a method for promoting hair growth, which includes administering the lactic acid bacteria-derived extracellular vesicle of an amount effective for preventing hair loss or promoting hair growth to a subject in need thereof.

In another aspect, the present disclosure provides the lactic acid bacteria-derived extracellular vesicle for preventing hair loss or promoting hair growth of a subject.

In another aspect, the present disclosure provides a use for preparing a composition containing the lactic acid bacteria-derived extracellular vesicle for preventing hair loss or promoting hair growth of a subject.

In an exemplary embodiment, the lactic acid bacteria-derived extracellular vesicle may be applied or administered to a subject in the form of a pharmaceutical composition, a cosmetic composition or a food composition.

In an exemplary embodiment, the lactic acid bacteria-derived extracellular vesicle may be applied or administered to the skin or scalp of a subject.

In an exemplary embodiment, the composition may be a freeze-dried formulation. The composition may be a freeze-dried formulation contained in a sealed packaging material or container so that it can be used readily (ready-to-use).

The present disclosure also provides a kit for preventing hair loss or promoting hair growth, which contains: a freeze-dried composition containing the lactic acid bacteria-derived extracellular vesicle as an active ingredient; and sterile water or purified water. The kit may be contained in a sealed packaging material or container so that it can be used readily (ready-to-use).

In an exemplary embodiment, the composition may be a pharmaceutical composition.

The pharmaceutical composition may contain, in addition to the lactic acid bacteria-derived extracellular vesicle, a pharmaceutical adjuvant such as an antiseptic, a stabilizer, a wetting agent, an emulsification promoter, a salt and/or buffer for control of osmotic pressure, etc. and other therapeutically useful substances and may be prepared into various formulations for oral or parenteral administration according to common methods.

The formulation for oral administration may be, for example, a tablet, a pill, a hard or soft capsule, a liquid, a suspension, an emulsion, a syrup, a powder, a dust, a fine granule, a granule, a pellet, etc. and these formulations may contain, in addition to the active ingredient, a surfactant, a diluent (e.g., lactose, dextrose, sucrose, mannitol, sorbitol, cellulose and glycine), a lubricant (e.g., silica, talc, stearic acid and a magnesium or calcium salt thereof and polyethylene glycol). The tablet may further contain a binder such as magnesium aluminum silicate, starch paste, gelatin, tragacanth, methyl cellulose, sodium carboxymethyl cellulose and polyvinylpyrrolidine and may contain a pharmaceutical additive such as a disintegrant, e.g., starch, agar or alginic acid or a sodium salt thereof, an absorbent, a colorant, a flavor, a sweetener, etc. as occasion demands. The tablet may be prepared by a common mixing, granulation or coating method.

The formulation for parenteral administration may be a formulation for transdermal administration, e.g., an injection, a drip, an ointment, a lotion, a gel, a cream, a spray, a suspension, an emulsion, a suppository, a patch, etc., although not being limited thereto.

Determination of the administration dosage of the active ingredient is within the level of those of ordinary skill. A daily administration dosage may vary depending on various factors such as the stage of the disease to be treated, age, health condition, presence of complication, etc. In an aspect, the composition may be administered at a daily dosage of 1 µg/kg to 200 mg/kg, more specifically 50 µg/kg to 50 mg/kg, 1-3 times a day. However, the administration dosage does not limit the scope of the present disclosure by any means.

The pharmaceutical composition may be a formulation for external application to the skin. The formulation for external application to the skin includes any formulation that can be applied externally on the skin and various types of medical formulations may be included therein.

In an exemplary embodiment, the composition may be a cosmetic composition.

The cosmetic composition may contain, in addition to the lactic acid bacteria-derived extracellular vesicle, a functional additive and an ingredient commonly included in a cosmetic composition. The functional additive may include an ingredient selected from a group consisting of a water-soluble vitamin, an oil-soluble vitamin, a polypeptide, a polysaccharide, a sphingolipid and a seaweed extract. In addition, an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a flavor, a blood circulation promoter, a cooling agent, an antiperspirant, purified water, etc. may be further contained.

The formulation of the cosmetic composition is not specially limited and may be selected adequately depending on purposes. For example, it may be prepared into one or more formulation selected from a group consisting of a skin lotion, a skin softener, a skin toner, an astringent, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion and a body cleanser, although not being limited thereto.

When the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

When the formulation of the present disclosure is a powder or a spray, lactose, talc, silica, aluminum hydroxide, calcium silicate, polyamide powder, etc. may be used as a carrier ingredient. In particular, when the formulation is a spray, it may further contain a propellant such as chlorofluorohydrocarbon, propane/butane or dimethyl ether.

When the formulation of the present disclosure is a solution or an emulsion, a solvent, a solubilizer or an emulsifier may be used as a carrier ingredient. For example, water, ethanol, isopropanol, ethyl carbonate, ethyl acetate, benzyl alcohol, benzyl benzoate, propylene glycol, 1,3-butyl glycol oil, a glycerol aliphatic ester, polyethylene glycol or a fatty acid ester of sorbitan may be used.

When the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the formulation of the present disclosure is a surfactant-containing cleanser, an aliphatic alcohol sulfate, an aliphatic alcohol ether sulfate, sulfosuccinic monoester, isethionate, an imidazolinium derivative, methyl taurate, sarcosinate, a fatty acid amide ether sulfate, an alkyl amidobetaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

In an exemplary embodiment, the composition may be a food composition.

The food composition may be a liquid or solid formulation. For example, it may be in the form of various foods, beverages, gums, teas, vitamin mixtures, supplementary health foods, etc. and may be formulated as a powder, a granule, a tablet, a capsule or a drink. Each formulation of the food composition may be prepared by those skilled in the art without difficulty by mixing the active ingredient with ingredients commonly used in the art depending on purposes. A synergic effect may be achieved when the active ingredient is used together with other ingredients.

Liquid ingredients that may be contained in the food composition in addition to the active ingredient are not particularly limited. Various flavors, natural carbohydrates, etc. may be further contained as in common drinks. The natural carbohydrate may be a monosaccharide, a disaccharide such as glucose, fructose, etc., a polysaccharide such as maltose, sucrose, etc., a common sugar such as dextrin, cyclodextrin, etc. or a sugar alcohol such as xylitol, sorbitol, erythritol, etc. As the flavor, a natural flavor (thaumatin, stevia extract (e.g., rebaudioside A, glycyrrhizin, etc.) or a synthetic flavor (e.g., saccharin, aspartame, etc.) may be used. The natural carbohydrate may be contained in an amount of generally about 1-20 g, specifically about 5-12 g, per 100 mL of the composition according to the present disclosure.

In an aspect, the food composition may contain various nutrients, vitamins, minerals (electrolytes), flavors such as synthetic flavors and natural flavors, colorants, extenders (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated drinks, etc. In another aspect, pulps for preparing natural fruit juice and vegetable drinks may be contained. These ingredients may be used independently or in combination. These additives may be used in an amount of about 0.001-20 parts by weight per 100 parts by weight of the composition according to the present disclosure, although not being limited thereto.

MODE FOR INVENTION

Hereinafter, the present disclosure will be described in detail through examples. However, the following examples are for illustrative purposes only and the scope of the present disclosure is not limited by the examples.

Example 1. Isolation of Lactic Acid Bacteria-Derived Extracellular Vesicles

Extracellular vesicles including exosome-like vesicles were isolated from lactic acid bacteria in the genus *Lactobacillus*. As the bacteria in the genus *Lactobacillus*, *Lactobacillus reuteri* (*L. reuteri*, KCTC 3594), *Lactobacillus rhamnosus* (*L. rhamnosus*, KCTC 5033) and *Lactobacillus sakei* (*L. sakei*, KCTC 3603) acquired from the Korean Collection for Type Cultures of the Korea Research Institute of Bioscience and Biotechnology.

(Step 1) A culture of lactic acid bacteria in the genus *Lactobacillus* was centrifuged at 4° C. and 1,800×g for 20 minutes in order to isolate and remove the bacteria in the genus *Lactobacillus* from the culture. That is to say, cells and a culture supernatant were separated by centrifuging at low speed.

(Step 2) The culture centrifuged in the step 1 was further centrifuged at 4° C. and 10,000×g for 20 minutes using a high-speed centrifuge in order to additionally remove cells, cell debris, etc.

(Step 3) The culture centrifuged in the step 2 was filtered through a 0.45-μm bottle-top filter in order to increase the purity of the culture.

(Step 4) The culture filtered in the step 3 was ultracentrifuged at 4° C. and 150,000×g for 3 hours to separate exosome-like vesicles.

(Step 5) After the ultracentrifugation in the step 4, the supernatant was removed and the remaining exosome-like vesicle pellets were resuspended in a buffer (HEPES buffer).

(Step 6) The exosome-like vesicles resuspended in the buffer in the step 5 were stored at −70° C. for use in the following tests.

Test Example 1. Measurement of Size of Lactic Acid Bacteria-Derived Extracellular Vesicles The size of the exosome-like vesicles isolated from the bacteria in the genus *Lactobacillus* obtained in Example 1 was analyzed by dynamic light scattering. The result is shown in FIG. 2.

As a result, it was confirmed that the exosome-like vesicles isolated from the bacteria in the genus *Lactobacillus* had an average diameter of 20-300 nm and were roughly spherical.

Test Example 2. Proliferation of Dermal Papilla Cells

Primary human dermal papilla cells (hDPCs) were treated with the exosome-like vesicles isolated from the bacteria in the genus *Lactobacillus* in Example 1 at various concentrations in order to investigate the effect of the lactic acid bacteria-derived extracellular vesicles on the proliferation of dermal papilla cells.

Specifically, the dermal papilla cells (hDPCs, passage 6, 7) were cultured (5% $CO_2$, 37° C.) on a 96-well plate with $2\times10^4$ cells/well for 24 hours and then treated with the exosome-like vesicles derived from the bacteria in the genus *Lactobacillus* at different concentrations (0.1-100 μg/mL). After culturing the cells for 48 hours, the culture medium was replaced and the effect on proliferation was evaluated by the MTT assay (100 μg/well, absorbance measured at 570 nm).

FIG. 3 shows the result of measuring the proliferation of the dermal papilla cells treated with the exosome-like vesicles at low concentrations (0.1-20 μg/mL), and FIGS. 4a and 4b show the result of measuring the proliferation of the dermal papilla cells treated with the exosome-like vesicles at high concentrations (10-100 μg/mL). In FIGS. 3, 4a and 4b, the ordinates indicate the proliferation of the dermal papilla cells (% relative to a negative control group (CTL)) and a 5% FBS positive control group was used for comparison. As a result, it was confirmed that the exosome-like vesicles derived from the bacteria in the genus *Lactobacillus* promote the proliferation of the dermal papilla cells.

Test Example 3. Hair Shaft Elongation

A hair follicle organ culture was treated with the exosome-like vesicles isolated from the bacteria in the genus *Lactobacillus* in Example 1 at various concentrations and the effect of the lactic acid bacteria-derived extracellular vesicles on hair shaft elongation was investigated.

Specifically, 12 hair follicles (isolated from 45-year-old and 63-year-old men) were tested 2 times per each test group. The hair follicles were cultured after treating with the exosome-like vesicles derived from the bacteria in the genus *Lactobacillus* at different concentrations (10-20 μg/mL). As a culture medium, William's E medium containing L-glutamine (2 mM), insulin (10 μL/mL), an antibiotic (1%), Fungizone (0.1%) and (−) hydrocortisone (10 ng/mL) was used. Hair length was measured while replacing the medium every 3 days. As a positive control, MNX (minoxidil) which is effective in preventing hair loss and promoting hair growth was used.

The effect on hair shaft elongation when the hair follicle organ culture was treated with the lactic acid bacteria-derived extracellular vesicles is shown in FIGS. 5 and 6. From FIGS. 5 and 6, it can be seen that the treatment with the exosome-like vesicles derived from the bacteria in the genus *Lactobacillus* leads to hair length increase.

Hereinafter, the present disclosure will be described in detail through formulation examples. However, the following formulation examples are for illustrative purposes only and the scope of the present disclosure is not limited by the formulation examples.

[Formulation Example 1] Soft Capsule

A soft capsule was prepared by mixing 50 mg of lactic acid bacteria-derived exosome-like vesicles of Example 1, 80-140 mg of L-carnitine, 180 mg of soybean oil, 2 mg of palm oil, 8 mg of hydrogenated vegetable oil, 4 mg of yellow beeswax and 6 mg of lecithin and filling 400 mg per capsule according to a commonly employed method.

[Formulation Example 2] Tablet

A tablet was prepared by mixing 50 mg of the lactic acid bacteria-derived exosome-like vesicles of Example 1, 200 mg of galactooligosaccharide, 60 mg of lactose and 140 mg of maltose, granulating the mixture using a fluidized-bed drier, adding 6 mg of sugar ester and then tableting using a tableting machine.

[Formulation Example 3] Granule

A granule was prepared by mixing 50 mg of the lactic acid bacteria-derived exosome-like vesicles of Example 1, 250 mg of anhydrous crystalline glucose and 550 mg of starch, granulating the mixture using a fluidized-bed granulator and then filling in a pouch.

[Formulation Example 4] Drink

A drink was prepared by mixing 50 mg of the lactic acid bacteria-derived exosome-like vesicles of Example 1, 10 g of glucose, 0.6 g of citric acid and 25 g of oligosaccharide syrup, adding 300 mL of purified water and filling 200 mL per bottle. After filling in the bottle, the drink was sterilized at 130° C. for 4-5 seconds.

[Formulation Example 5] Ointment

An ointment was prepared with the composition described in Table 1 according to a commonly employed method.

TABLE 1

| Ingredients | Contents (wt %) |
| --- | --- |
| Lactic acid bacteria-derived exosome-like vesicles of Example 1 | 2.00 |
| Glycerin | 8.00 |

TABLE 1-continued

| Ingredients | Contents (wt %) |
|---|---|
| Butylene glycol | 4.00 |
| Liquid paraffin | 15.00 |
| β-Glucan | 7.00 |
| Carbomer | 0.10 |
| Caprylic/capric triglyceride | 3.00 |
| Squalane | 1.00 |
| Cetearyl glucoside | 1.50 |
| Sorbitan stearate | 0.40 |
| Cetearyl alcohol | 1.00 |
| Beeswax | 4.00 |
| Purified water | balance |
| Total | 100.00 |

[Formulation Example 6] Beauty Solution

A beauty solution was prepared with the composition described in Table 2 according to a commonly employed method.

TABLE 2

| Ingredients | Contents (wt %) |
|---|---|
| Lactic acid bacteria-derived exosome-like vesicles of Example 1 | 2.00 |
| Hydroxyethyl cellulose (2% aqueous solution) | 12.00 |
| Xanthan gum (2% aqueous solution) | 2.00 |
| 1,3-Butylene glycol | 6.00 |
| Thick glycerin | 4.00 |
| Sodium hyaluronate (1% aqueous solution) | 5.00 |
| Purified water | balance |
| Total | 100.00 |

[Formulation Example 7] Shampoo

A shampoo solution was prepared with the composition described in Table 3 according to a commonly employed method.

TABLE 3

| Ingredients | Contents (wt %) |
|---|---|
| Lactic acid bacteria-derived exosome-like vesicles of Example 1 | 2.00 |
| Sodium lauryl sulfate | 10.00 |
| Cocamidopropyl betaine | 3.00 |
| Carboxyvinyl polymer | 0.30 |
| Polyquaternium-10 | 0.20 |
| Cetyltrimethylammonium chloride | 0.10 |
| Purified water | balance |
| Total | 100.00 |

[Formulation Example 8] Rinse

A rinse was prepared with the composition described in Table 4 according to a commonly employed method.

TABLE 4

| Ingredients | Contents (wt %) |
|---|---|
| Lactic acid bacteria-derived exosome-like vesicles of Example 1 | 2.00 |
| Cetyl alcohol | 2.00 |
| Stearyl alcohol | 2.50 |
| Behenyl alcohol | 0.50 |
| Silicone emulsion | 0.40 |
| Cyclomethicone | 1.00 |
| Dimethyldistearylammonium chloride | 0.10 |
| Purified water | balance |
| Total | 100.00 |

While the exemplary embodiments have been shown and described, it will be understood by those skilled in the art that various changes in form and details may be made thereto without departing from the spirit and scope of this disclosure as defined by the appended claims.

We claim:

1. A method for promoting hair growth, comprising administering an effective amount of extracellular vesicles isolated from lactic acid bacteria for promoting hair growth to a subject in need thereof;
wherein the lactic acid bacterium comprises a bacterium in the genus *Lactobacillus* and wherein the extracellular vesicles are administered at a concentration of 0.1-100 μg/mL.

2. The method according to claim 1, wherein the bacterium in the genus *Lactobacillus* comprises one or more selected from the group consisting of *Lactobacillus reuteri* (*L. reuteri*), *Lactobacillus rhamnosus* (*L. rhamnosus*) and *Lactobacillus sakei* (*L. sakei*).

3. The method according to claim 1, wherein the extracellular vesicle is isolated from a culture of lactic acid bacteria.

4. The method according to claim 1, wherein the extracellular vesicle is an exosome-like vesicle.

5. The method according to claim 1, wherein the extracellular vesicle has a diameter of 20-500 nm.

6. The method according to claim 1, wherein the extracellular vesicle precipitates when a culture of lactic acid bacteria is ultracentrifuged at 100,000×g or higher.

7. The method according to claim 1, wherein the extracellular vesicle induces hair growth by activating dermal papilla cells (DPCs).

* * * * *